US00PP21800P2

(12) United States Plant Patent
Murakami

(10) Patent No.: US PP21,800 P2
(45) Date of Patent: Mar. 22, 2011

(54) ***SISYRINCHIUM* PLANT NAMED 'SUNSISIKI'**

(50) Latin Name: *Sisyrinchium atlanticum*
Varietal Denomination: Sunsisiki

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/590,018

(22) Filed: Oct. 30, 2009

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—June Hwu
(74) *Attorney, Agent, or Firm*—C. A. Whealy

(57) ABSTRACT

A new and distinct cultivar of *Sisyrinchium* plant named 'Sunsisiki', characterized by its compact and clumping plant habit; vigorous growth habit; freely flowering plant habit; long flowering period; light yellow-colored flowers with purple-colored centers and venation; and good garden performance.

1 Drawing Sheet

Botanical designation: *Sisyrinchium atlanticum.*
Cultivar denomination: 'SUNSISIKI'.

BACKGROUND OF THE INVENTION

The present invention relates to a new and distinct cultivar of *Sisyrinchium* plant, botanically known as *Sisyrinchium atlanticum* and hereinafter referred to by the name 'Sunsisiki'.

The new *Sisyrinchium* plant is a product of a planned breeding program conducted by the Inventor in Higashiomi, Shiga, Japan. The objective of the breeding program is to develop new freely-flowering *Sisyrinchium* plants with attractive and unique flower coloration and long flowering period.

The new *Sisyrinchium* plant originated from a cross-pollination conducted by the Inventor in Higashiomi, Shiga, Japan in May, 2002 of a proprietary selection of *Sisyrinchium atlanticum* identified as code number SC6, not patented, as the female, or seed, parent with a proprietary selection of *Sisyrinchium atlanticum* identified as code number SC5, not patented, as the male, or pollen, parent. The new *Sisyrinchium* plant was discovered and selected by the Inventor as a single flowering plant from within the progeny of the stated cross-pollination in a controlled greenhouse environment in Higashiomi, Shiga, Japan in August, 2003.

Asexual reproduction of the new *Sisyrinchium* plant by divisions in a controlled greenhouse environment in Higashiomi, Shiga, Japan since September, 2003, has shown that the unique features of this new *Sisyrinchium* plant are stable and reproduced true to type in successive generations.

SUMMARY OF THE INVENTION

Plants of the new *Sisyrinchium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunsisiki'.

These characteristics in combination distinguish 'Sunsisiki' as a new and distinct cultivar of *Sisyrinchium:*

1. Compact and clumping plant habit.
2. Vigorous growth habit.
3. Freely flowering plant habit.
4. Long flowering period.
5. Light yellow-colored flowers with purple-colored centers and venation.
6. Good garden performance.

Plants of the new *Sisyrinchium* can be compared to plants of the female parent selection. Plants of the new *Sisyrinchium* differ primarily from plants of the female parent selection in the following characteristics:

1. Plants of the new *Sisyrinchium* are more freely flowering than plants of the female parent selection.
2. Plants of the new *Sisyrinchium* flower for a longer period of time than plants of the female parent selection.
3. Plants of the new *Sisyrinchium* and the female parent selection differ in flower color as plants of the female parent selection have violet blue-colored flowers with purple-colored centers.

Plants of the new *Sisyrinchium* can be compared to plants of the male parent selection. Plants of the new *Sisyrinchium* differ primarily from plants of the male parent selection in the following characteristics:

1. Plants of the new *Sisyrinchium* are more freely flowering than plants of the male parent selection.
2. Plants of the new *Sisyrinchium* flower for a longer period of time than plants of the male parent selection.
3. Plants of the new *Sisyrinchium* and the male parent selection differ in flower color as plants of the male parent selection have ivory-colored flowers with purple-colored centers.

Plants of the new *Sisyrinchium* can also be compared to plants of *Sisyrinchium californicum* 'Yellow Stone', not patented. In side-by-side comparisons conducted in Higashiomi, Shiga, Japan, plants of the new *Sisyrinchium* and 'Yellow Stone' differed primarily in the following characteristics:

1. Plants of the new *Sisyrinchium* were more vigorous than plants of 'Yellow Stone'.

2. Plants of the new *Sisyrinchium* had thinner but more branching stems than plants of 'Yellow Stone'.
3. Plants of the new *Sisyrinchium* had smaller basal leaves than plants of 'Yellow Stone'.
4. Plants of the new *Sisyrinchium* were more freely flowering than plants of 'Yellow Stone'.
5. Plants of the new *Sisyrinchium* flowered earlier and for a longer period of time than plants of 'Yellow Stone'.
6. Plants of the new *Sisyrinchium* and 'Yellow Stone' differed in flower color as plants of 'Yellow Stone' had darker yellow-colored flowers.

BRIEF DESCRIPTION OF THE PHOTOGRAPHS

The accompanying colored photographs illustrate the overall appearance of the new *Sisyrinchium*, showing the colors as true as it is reasonably possible to obtain in colored reproductions of this type. Colors in the photographs may differ slightly from the color values cited in the detailed botanical description which accurately describe the colors of the new *Sisyrinchium*.

The photograph at the top of the sheet comprises a side perspective view of a typical flowering plant of 'Sunsisiki' grown in a container.

The photograph at the bottom of the sheet is a close-up view of typical flowers of 'Sunsisiki'.

DETAILED BOTANICAL DESCRIPTION

The aforementioned photographs and following observations, measurements and values describe plants grown in 15-cm containers in Higashiomi, Shiga, Japan, under commercial practice during the spring and early summer in an outdoor nursery. During the production of the plants, day temperatures averaged 23° C. and night temperatures averaged 13° C. Plants were six and five months old when the description and photographs, respectively, were taken. In the following description, color references are made to The Royal Horticultural Society Colour Chart, 2001 Edition, except where general terms of ordinary dictionary significance are used.

Botanical classification: *Sisyrinchium atlanticum* 'Sunsisiki'.

Parentage:

*Female, or seed, parent.*—Proprietary selection of *Sisyrinchium atlanticum* identified as code number SC6, not patented.

*Male, or pollen, parent.*—Proprietary selection of *Sisyrinchium atlanticum* identified as code number SC5, not patented.

Propagation:

*Type.*—By divisions.

*Time to initiate roots, summer.*—About one week at 20° C. to 30° C.

*Time to initiate roots, winter.*—About two weeks at 10° C. to 20° C.

*Time to produce a rooted young plant, summer.*—About three weeks at 20° C. to 30° C.

*Time to produce a rooted young plant, winter.*—About four weeks at 10° C. to 20° C.

*Root description.*—Fibrous; white in color.

*Rooting habit.*—Freely branching; moderately dense.

Plant description:

*Plant and growth habit.*—Compact and clumping plant habit; basally branching; vigorous growth habit.

*Plant height.*—About 34 cm.

*Plant diameter.*—About 51 cm.

Branch description:

*Length.*—Primary branches, about 21 cm; secondary branches, about 6.3 cm.

*Diameter, primary and secondary branches.*—About 1.2 mm.

*Strength.*—Strong.

*Aspect.*—Upright to somewhat outwardly.

*Texture.*—Smooth, glabrous.

*Color.*—Close to 146B.

Foliage description:

*Arrangement.*—Basal or cauline, simple; sessile.

*Basal leaves.*—Length: About 10.4 cm. Width: About 4 mm.

*Upper, or stem, leaves.*—Length: About 9.1 cm. Width: About 5 mm.

*Shape, basal and stem leaves.*—Lanceolate.

*Apex, basal and stem leaves.*—Acute.

*Base, basal and stem leaves.*—Sheathing.

*Margin, basal and stem leaves.*—Entire.

*Texture, basal and stem leaves, upper and lower surfaces.*—Smooth, glabrous.

*Venation pattern, basal and stem leaves.*—Parallel.

*Color, basal and stem leaves.*—Developing leaves, upper and lower surfaces: Close to 143C. Fully expanded leaves, upper and lower surfaces: Close to 143C; venation, close to 143D.

Flower description:

*Flower arrangement and habit.*—Four or five star-shaped flowers arranged in clusters; freely flowering habit with usually about 51 flowers developing per plant; flowers face upright.

*Fragrance.*—None detected.

*Natural flowering season.*—Early flowering habit, plants of the new *Sisyrinchium* initiate and develop flowers about 13 weeks after planting; long flowering period, flowering commences naturally during the spring and plants flower continuously throughout the summer until autumn in Japan.

*Flower longevity.*—Individual flowers last about one day on the plant; flowers persistent.

*Flower cluster height.*—About 13 cm.

*Flower cluster diameter.*—About 6.9 cm.

*Flower diameter.*—About 2.2 cm.

*Flower length (depth).*—About 1.2 cm.

*Flower bud.*—Shape: Oblong. Length: About 6.8 mm. Diameter: About 1.4 mm. Color: Close to 9D.

*Corolla.*—Arrangement: Six segments in a single whorl fused at the base. Segment length from throat: About 10.2 mm. Segment width: About 5.8 mm. Segment shape: Ovate. Segment apex: Cuspidate. Segment margin: Entire. Segment texture, upper and lower surfaces: Smooth, glabrous. Segment color: When opening, upper surface: Close to 3A; towards the center, close to 79A; venation, close to N77D; center, close to 7A. When opening, lower surface: Close to 3B; towards the base, close to 7B; venation, close to N79A. Fully opened, upper surface: Close to 3D; towards the center, close to 79B; venation, close to N77D; center, close to 7A. Fully opened, lower surface: Close to 3D; towards the base, close to 7B; venation, close to N79D.

*Spathe bracts.*—Quantity: Two per flower. Length: About 2.7 cm. Width: About 2.6 mm. Shape: Lanceolate. Apex: Acute. Margin: Entire. Texture, upper and lower surfaces: Smooth, glabrous. Color, immature, upper and lower surfaces: Close to 146B. Color, mature, upper and lower surfaces: Close to 146B.

*Pedicels.*—Length: About 2.7 cm. Diameter: About 0.4 mm. Angle: Mostly upright. Strength: Strong, wiry. Texture: Smooth, glabrous. Color: Close to N199C to N199D.

*Reproductive organs.*—Stamens: Quantity/arrangement: Three per flower; fused. Stamen length: About 1.3 mm. Anther shape: Globose. Anther size: About 0.9 mm by 0.9 mm. Anther color: Close to 13A. Pollen amount: Moderate. Pollen color: Close to 13A. Pistils: Quantity: One per flower. Pistil length: About 4.4 mm. Style color: Close to 154C. Stigma shape: Trifid. Stigma color: Close to 154D. Ovary color: Close to 144A. Seed/fruit: Seed and fruit development have not been observed on plants of the new *Sisyrinchium.*

Garden performance: Plants of the new *Sisyrinchium* have been observed to have good garden performance and to tolerate wind, rain and temperatures ranging from about −5° C. to about 35° C.

Pathogen/pest resistance: Plants of the new *Sisyrinchium* have not been observed to be resistant to pests and pathogens common to *Sisyrinchium.*

It is claimed:

1. A new and distinct *Sisyrinchium* plant named 'Sunsisiki' as illustrated and described.

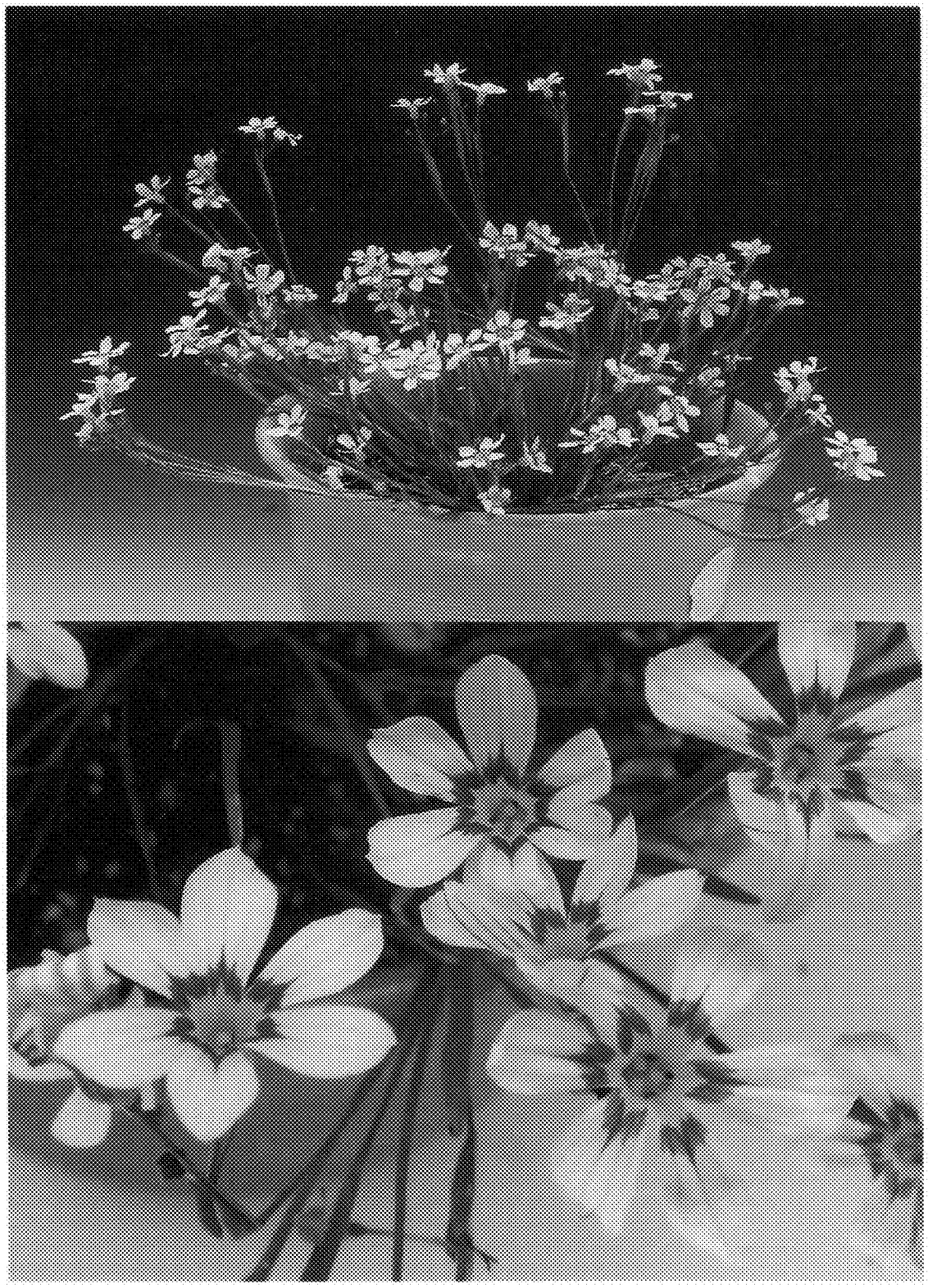

* * * * *